(12) United States Patent
Poole

(10) Patent No.: US 11,865,223 B2
(45) Date of Patent: Jan. 9, 2024

(54) TRANSACTIONAL CURRENCY SANITIZER

(71) Applicant: David Alan Poole, Qualicum Beach (CA)

(72) Inventor: David Alan Poole, Qualicum Beach (CA)

(*) Notice: Subject to any disclaimer, the term of this patent is extended or adjusted under 35 U.S.C. 154(b) by 543 days.

(21) Appl. No.: 17/140,554

(22) Filed: Jan. 4, 2021

(65) Prior Publication Data

US 2022/0016291 A1 Jan. 20, 2022

Related U.S. Application Data

(60) Provisional application No. 63/052,648, filed on Jul. 16, 2020.

(51) Int. Cl.
| | |
|---|---|
| *A61L 2/26* | (2006.01) |
| *G07D 11/14* | (2019.01) |
| *G07D 11/50* | (2019.01) |
| *G07D 11/40* | (2019.01) |
| *G07D 11/125* | (2019.01) |
| *A61L 2/10* | (2006.01) |
| *G07D 7/1205* | (2016.01) |
| *G06V 20/10* | (2022.01) |

(52) U.S. Cl.
CPC .................... *A61L 2/26* (2013.01); *A61L 2/10* (2013.01); *G07D 7/1205* (2017.05); *G07D 11/125* (2019.01); *G07D 11/14* (2019.01); *G07D 11/40* (2019.01); *G07D 11/50* (2019.01); *A61L 2202/11* (2013.01); *A61L 2202/122* (2013.01); *G06V 20/10* (2022.01); *G07D 2207/00* (2013.01); *G07D 2211/00* (2013.01)

(58) Field of Classification Search
CPC .. A61L 2/26; A61L 2202/11; A61L 2202/122; G07D 7/1205; G07D 2207/00; G07D 2211/00; G07D 11/50; G07D 11/125; G07D 11/40; G07D 11/14; G06V 20/10
See application file for complete search history.

(56) References Cited

U.S. PATENT DOCUMENTS

2011/0243789 A1 10/2011 Roberts

*Primary Examiner* — Nicole M Ippolito
*Assistant Examiner* — Hanway Chang
(74) *Attorney, Agent, or Firm* — Nexus Law Group LLP; Nicholas P. Toth

(57) ABSTRACT

A transactional currency sanitizer which includes an enclosure, a deposit device on the enclosure for depositing the currency into said enclosure, an ultraviolet radiation-producing (UV) device with at least two spaced-apart UV light emitters, and a retrieval device on the enclosure for retrieving the currency from said enclosure. The deposit device is configured to receive the currency and pass the currency between the at least two spaced-apart UV light emitters to sanitize both sides of the currency and the retrieval device is configured to accept the sanitized currency from between said device at least two spaced-apart UV light emitters and to provide the sanitized currency for retrieval from said enclosure.

27 Claims, 17 Drawing Sheets

TRANSACTIONAL CURRENCY SANITIZER

COPYRIGHT NOTICE

This patent document contains material which is subject to copyright protection. The copyright owner has no objection to the facsimile reproduction by anyone of this patent document as it appears in the Patent and Trademark Office patent file or records, but otherwise reserves all copyright rights whatsoever.

FIELD OF THE INVENTION

The invention relates to a sanitizing machine for the sanitary cleaning of currency.

BACKGROUND OF THE INVENTION

In recent society, there has been a trend toward increased sanitization of everyday objects and surfaces one tends to come in contact with. This trend is evidenced by a quick trip to one's local store where one will find the shelves lined with antibacterial soap, hand lotion sanitizer, anti-bacterial surface cleaner, HEPA air filtration systems and the like. At the same time, pandemics such as COVID-19, are becoming more and more common further reinforcing the importance of reduced contact with common surfaces and items. Finally, there is perhaps no greater common item than paper currency which is touched, carried, and transferred amongst almost all of the worlds' population. Accordingly, there exists a need for a means by which paper-based currency can be sanitized to address the problems as described above. The use of the transactional currency sanitizer allows for the sterilization and cleaning of currency in a manner which is quick, easy, and effective.

Accordingly, a need exists for a transactional currency sanitizer. Other objects of the invention will be apparent from the description that follows.

SUMMARY OF THE INVENTION

According to the present invention there is provided a transactional currency sanitizer. The sanitizer includes an enclosure, a deposit device on the enclosure for depositing the currency into the enclosure, an ultraviolet radiation-producing (UV) device inside of the enclosure, which has at least two spaced-apart UV light emitters and a retrieval device on the enclosure for retrieving the currency from the enclosure.

The deposit device may be configured to receive the currency and pass the currency between the at least two spaced-apart UV light emitters to sanitize both sides of the currency. The retrieval device may be configured to accept the sanitized currency from between the at least two spaced-apart UV light emitters and to provide the sanitized currency for retrieval from the enclosure.

The deposit device may include an opening on the enclosure and a deposit chute cooperating with the opening and operable to pass the currency between the at least two spaced-apart UV light emitters. Alternatively, the deposit device may include an opening on the enclosure and a deposit roller system cooperating with the opening and operable to pass the currency between the at least two spaced-apart UV light emitters.

The retrieval device may include an exit on the enclosure and a retrieval chute linearly aligned with the deposit chute and opposite from the UV device. The retrieval chute may be operable to retrieve the sanitized currency after exiting the UV device and providing the sanitized currency to the exit. Alternatively, the retrieval device may include an exit on the enclosure and a retrieval roller system linearly aligned with the deposit roller system and opposite from the UV device. The retrieval roller system may be operable to retrieve the sanitized currency after exiting the UV device and providing the sanitized currency to the exit.

Each of the deposit and retrieval roller systems may be configured to accept multiple pieces of currency.

The transactional currency sanitizer may also include a currency calculator inside of the said enclosure. The currency calculator may include a high-speed camera in communication with a processor which may include artificial intelligence (AI) software operable to determine various denominations of currency and operable to calculate a total value of currency being sanitized. The AI software may also be operable to detect counterfeit currency.

The exit may include a collection drawer operable in two states. In the first state, it may be open for a user to open and retrieve the sanitized currency; in the second state, it may be closed state to safely store the sanitized currency inside the enclosure. The collection drawer may include a locking device.

The transactional currency sanitizer may also include a service door for maintenance of the currency sanitizer. The service door may be configured for locking and unlocking.

The transactional currency sanitizer may also include a WiFi transponder in communication with the processor. The sanitizer may also include an exterior controller in communication with the processor for operating the currency sanitizer. The controller may be a touch screen device.

In another embodiment of the invention, there is provided a transactional currency sanitizer which includes a bill sanitizer, a coin sanitizer, an ultraviolet radiation-producing (UV) device with at least two spaced-apart UV light emitters, at least one collection drawer, and an enclosure.

The bill sanitizer may capable of directing an individual bill of currency through the at least two spaced-apart UV light emitters to sanitize both sides of the individual bill of currency and it may be capable of depositing said the individual bill of currency into an individual collection drawer.

The coin sanitizer may be capable of directing an individual coin of currency through the at least two spaced-apart UV light emitters to sanitize both sides of the individual coin of currency and it may be capable of depositing the individual coin of currency into another individual collection drawer.

Other aspects of the invention will be appreciated by reference to the detailed description of the preferred embodiment and to the claims that follow.

BRIEF DESCRIPTION OF THE DRAWINGS

The preferred embodiment of the invention will be described by reference to the drawings thereof in which.

DESCRIPTION OF THE PREFERRED EMBODIMENT OF THE INVENTION

Figure 1:
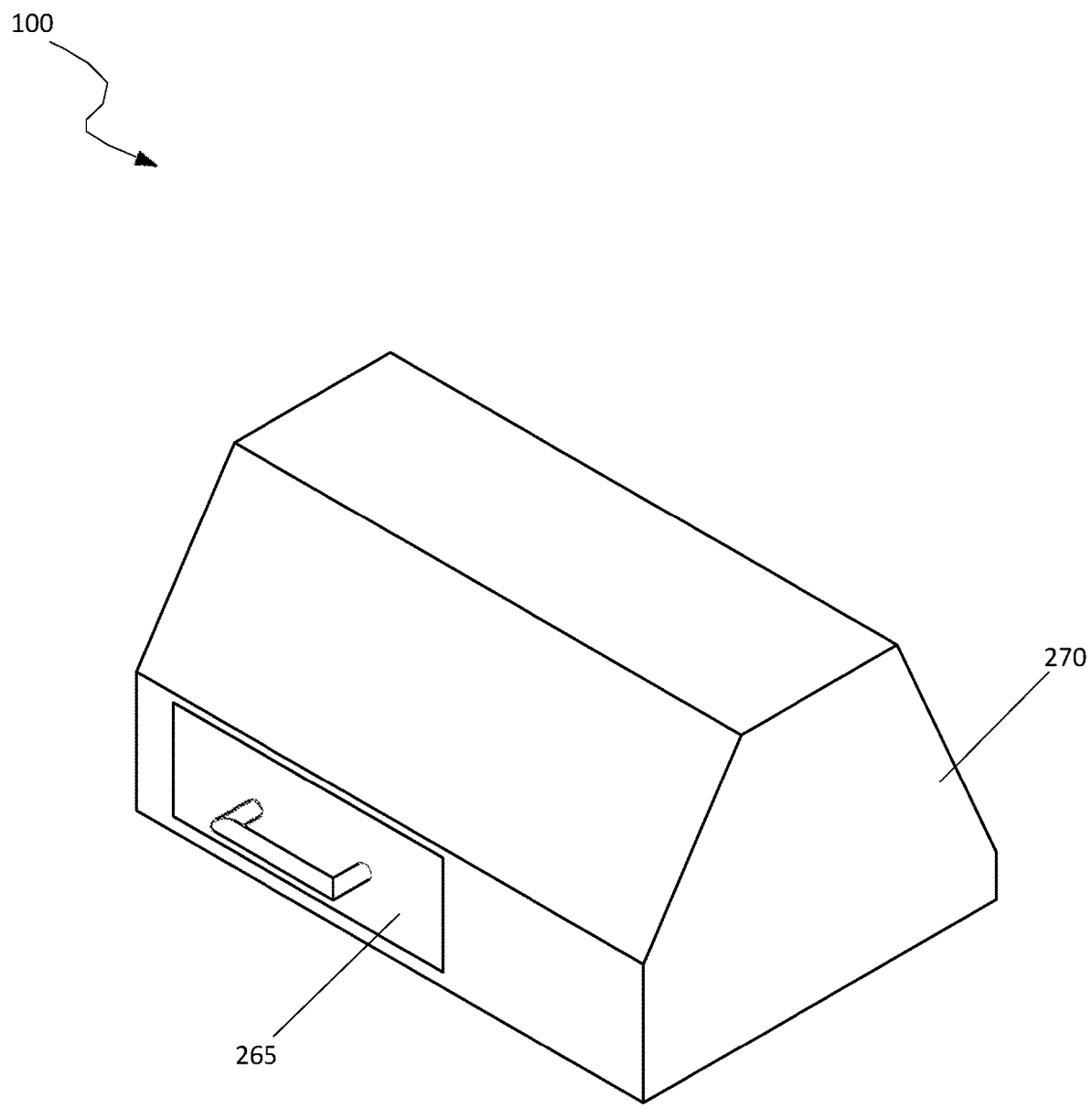
FIG. 1 is an isometric view of a transactional money sanitizer according to an embodiment of the present invention.
Figure 2:
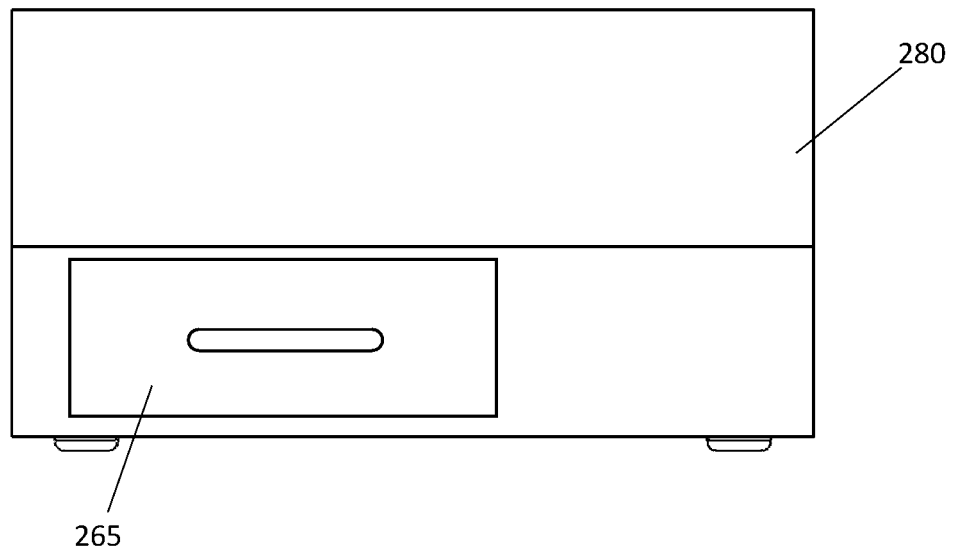
FIG. 2 is a front view of a transactional money sanitizer, according to an embodiment of the present invention.
Figure 3:
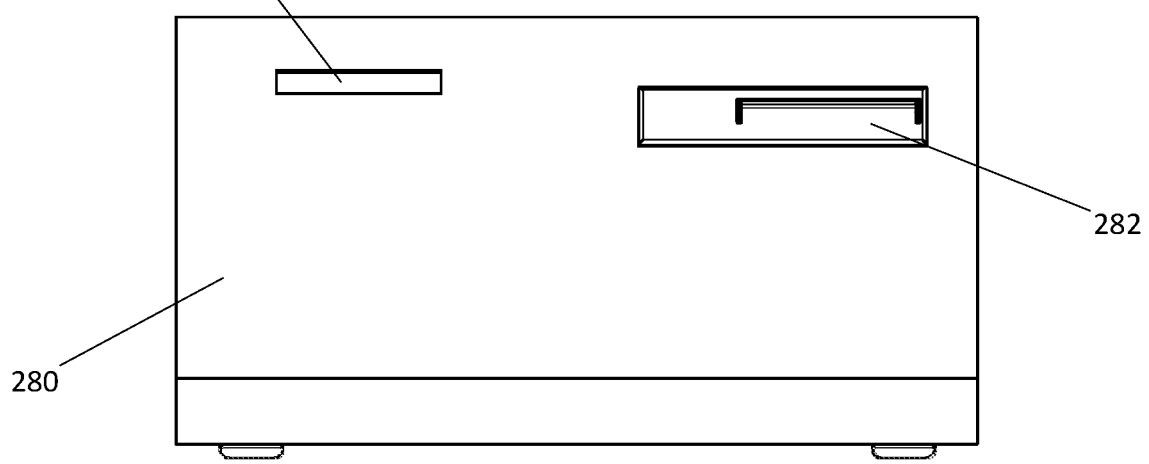
FIG. 3 is a rear view of a transactional money sanitizer, according to an embodiment of the present invention.
Figure 4:
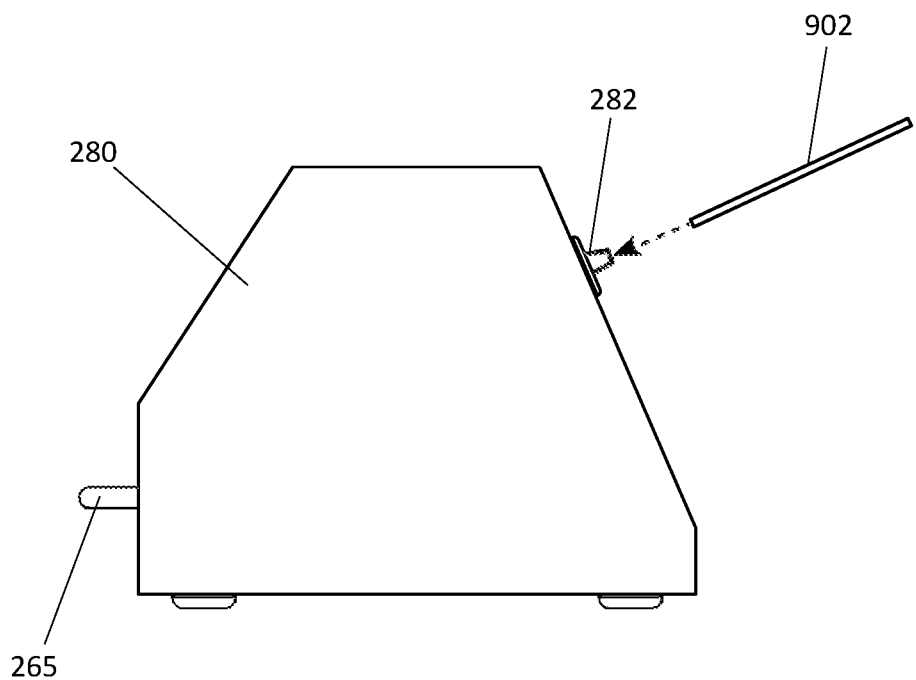
FIG. 4 is a side view of a transactional money sanitizer, according to an embodiment of the present invention.
Figure 5:
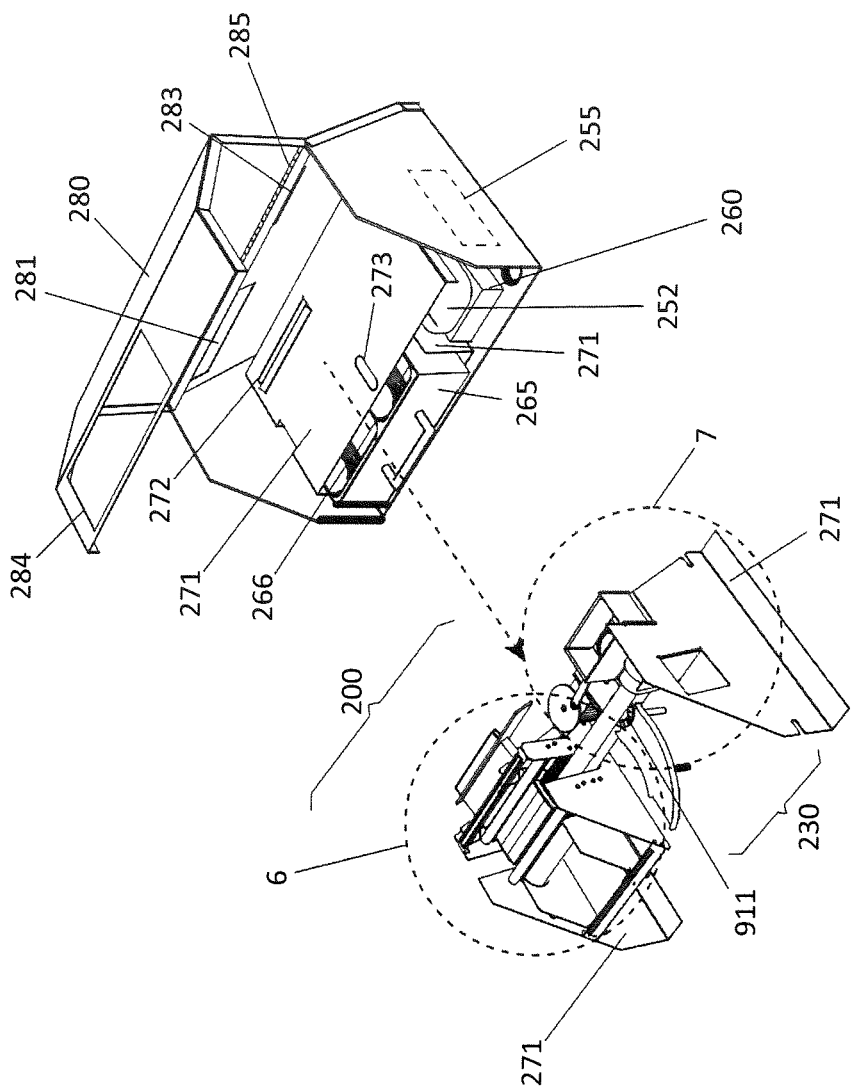
FIG. 5 is an exploded rear view of a transactional money sanitizer, according to an embodiment of the present invention.
Figure 6:
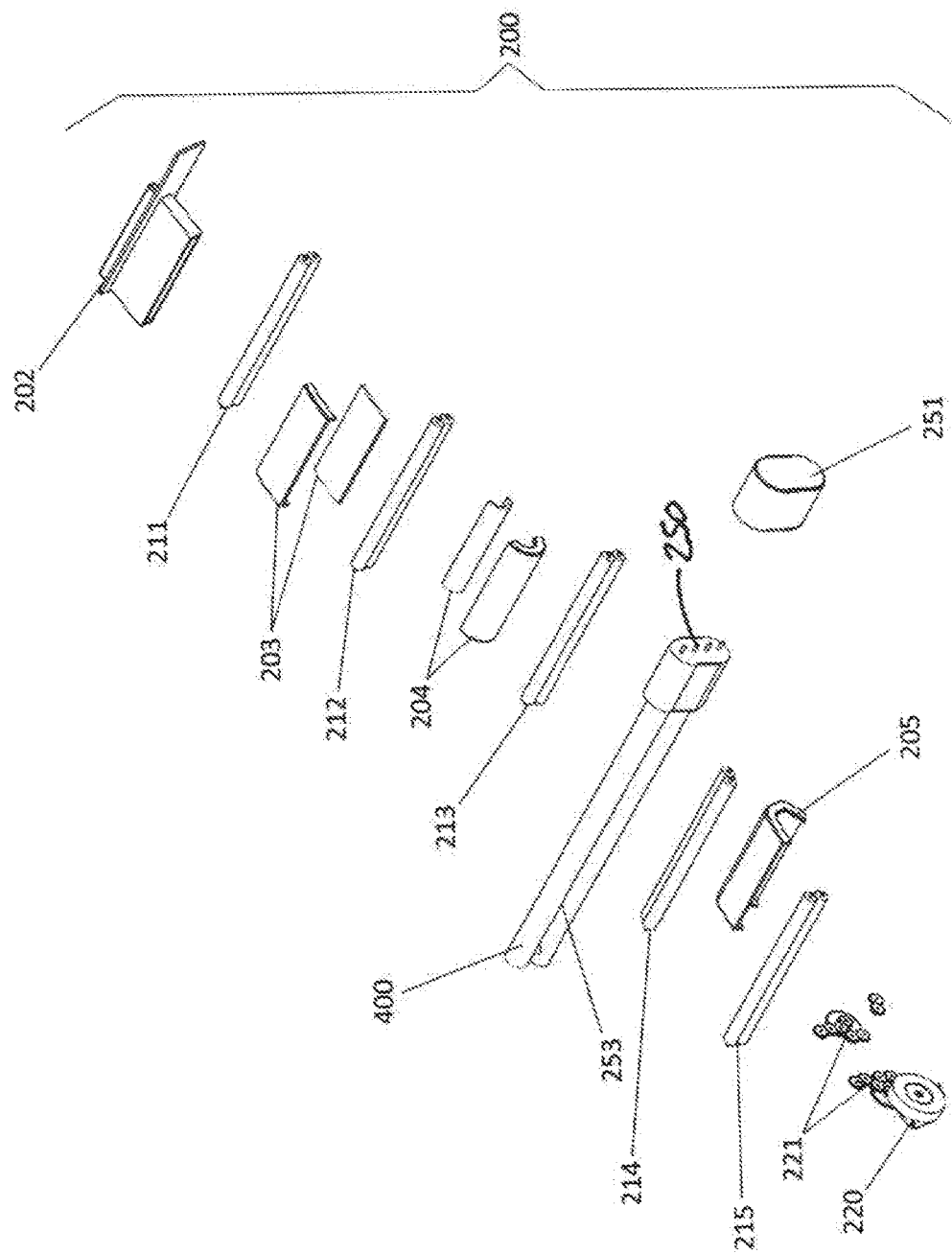
FIG. 6 is a detail view of a transactional money sanitizer, according to an embodiment of the present invention illustrating components of the area marked 6 in FIG. 5.
Figure 7:
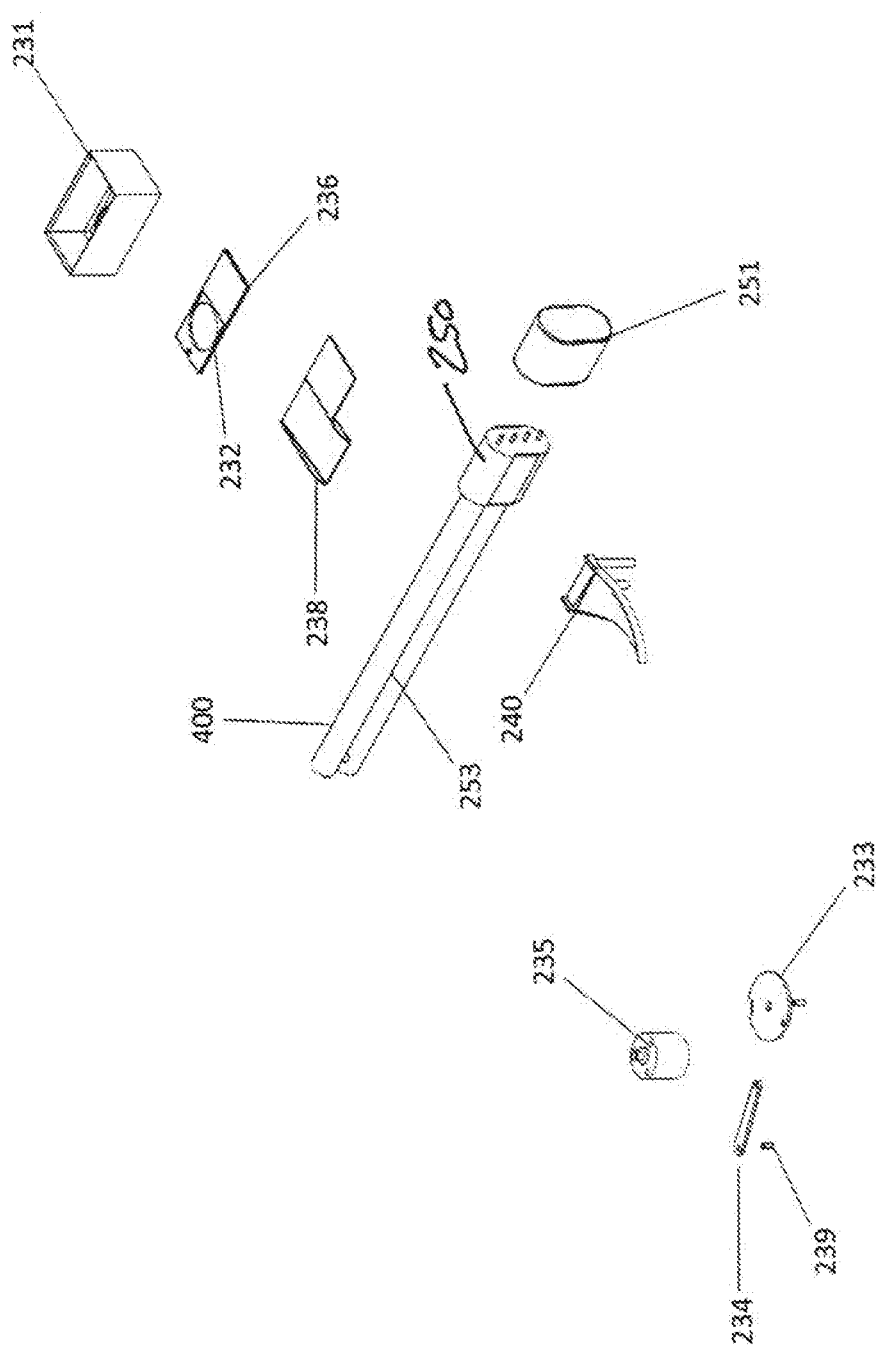
FIG. 7 is a detail view of a transactional money sanitizer, according to an embodiment of the present invention illustrating components of the area marked 7 in FIG. 5.
Figure 8:
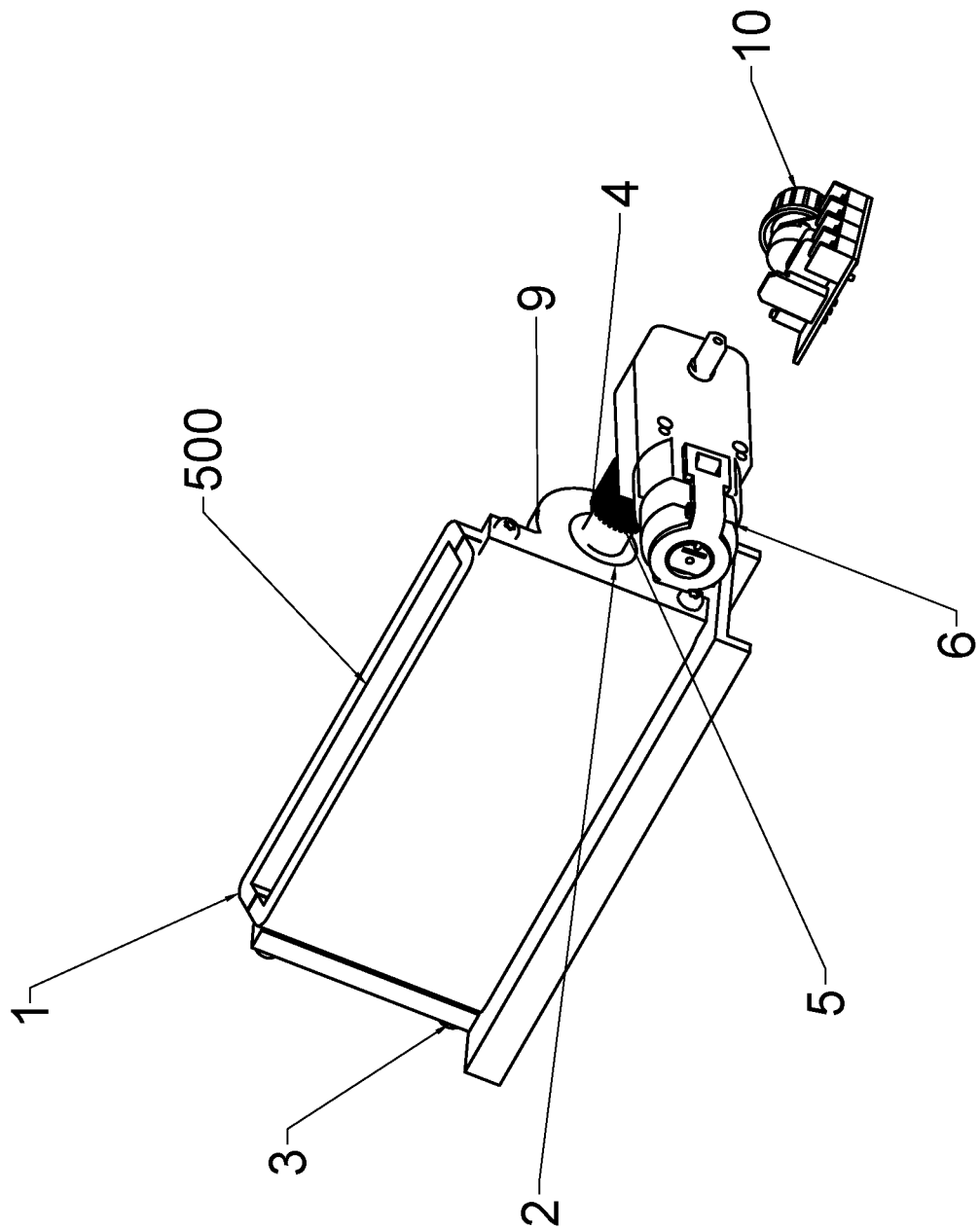
FIG. 8 is an isometric view of a roller system of the transactional money sanitizer according to an embodiment of the present invention.
Figure 9:
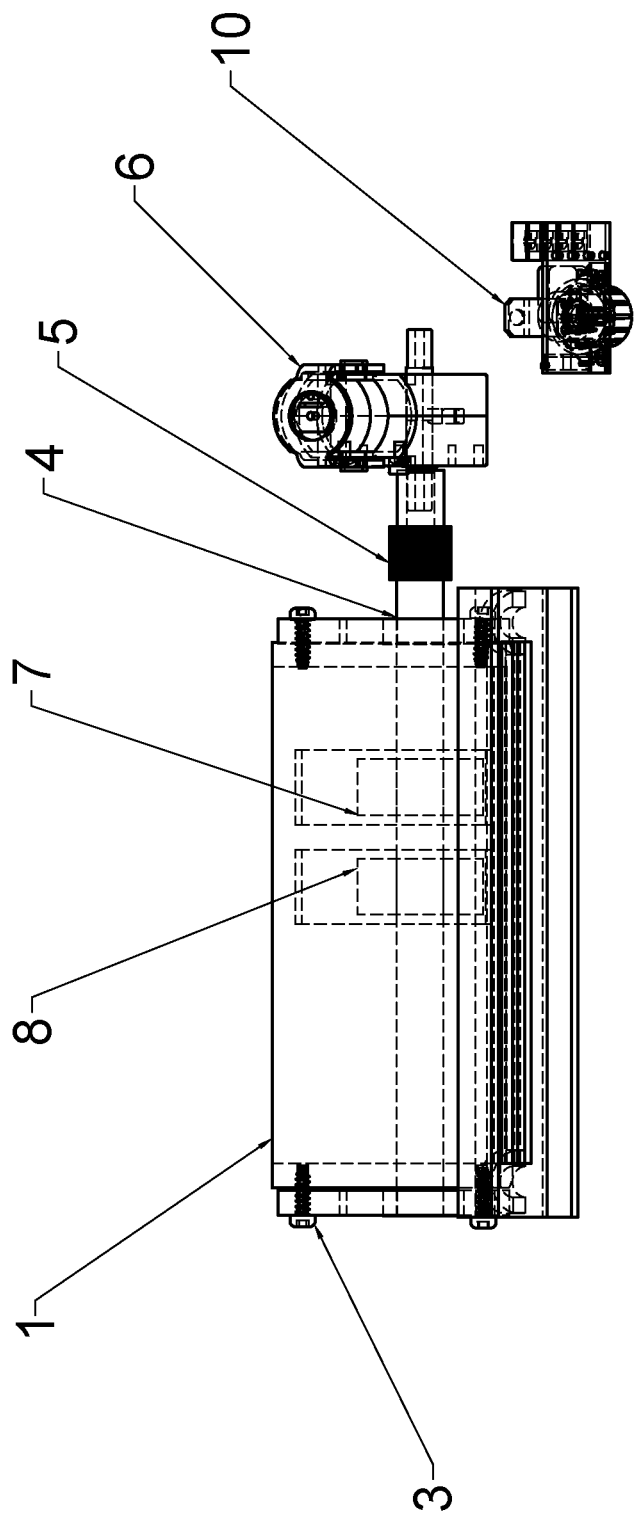
FIG. 9 is a front view showing hidden lines of the roller system of the transactional money sanitizer showing according to an embodiment of the present invention.
Figure 10:
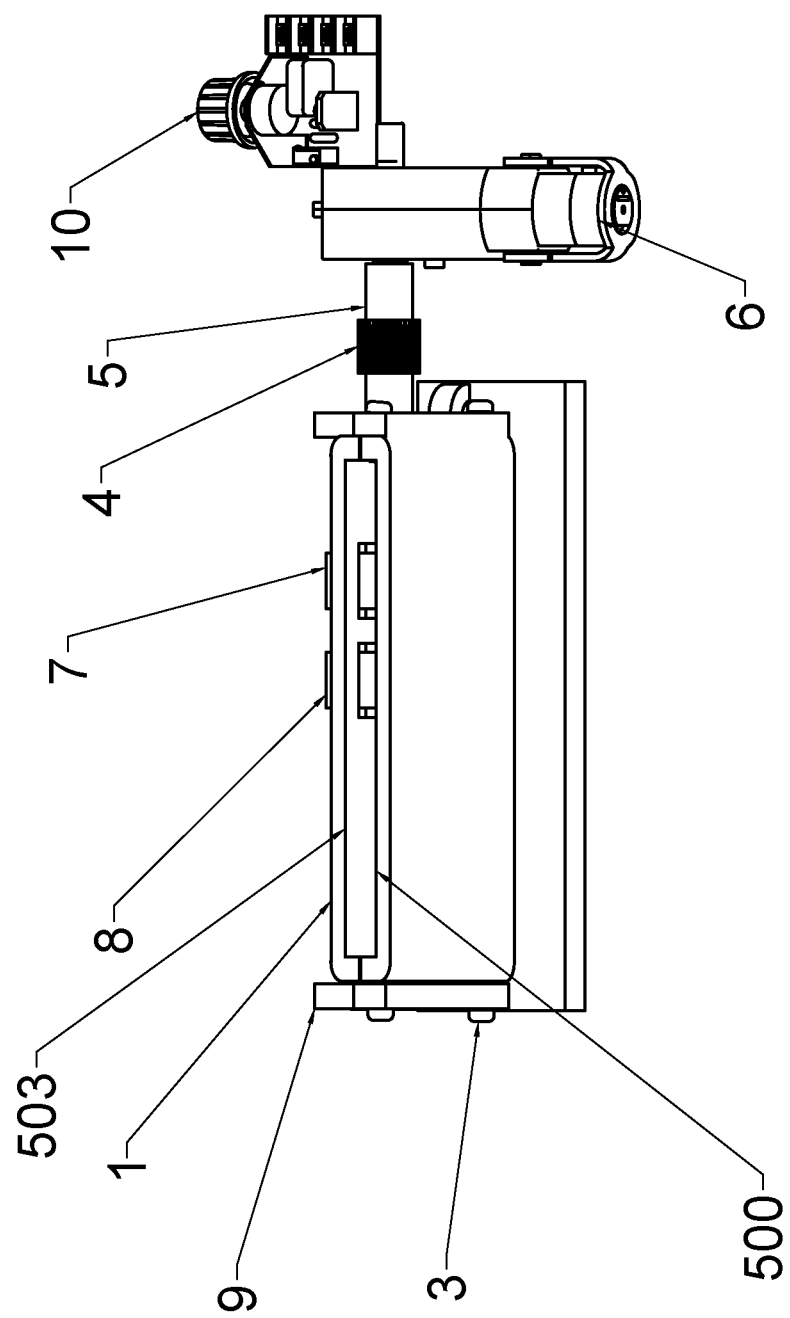
FIG. 10 is a top view the roller system of the transactional money sanitizer showing according to an embodiment of the present invention.
Figure 11:
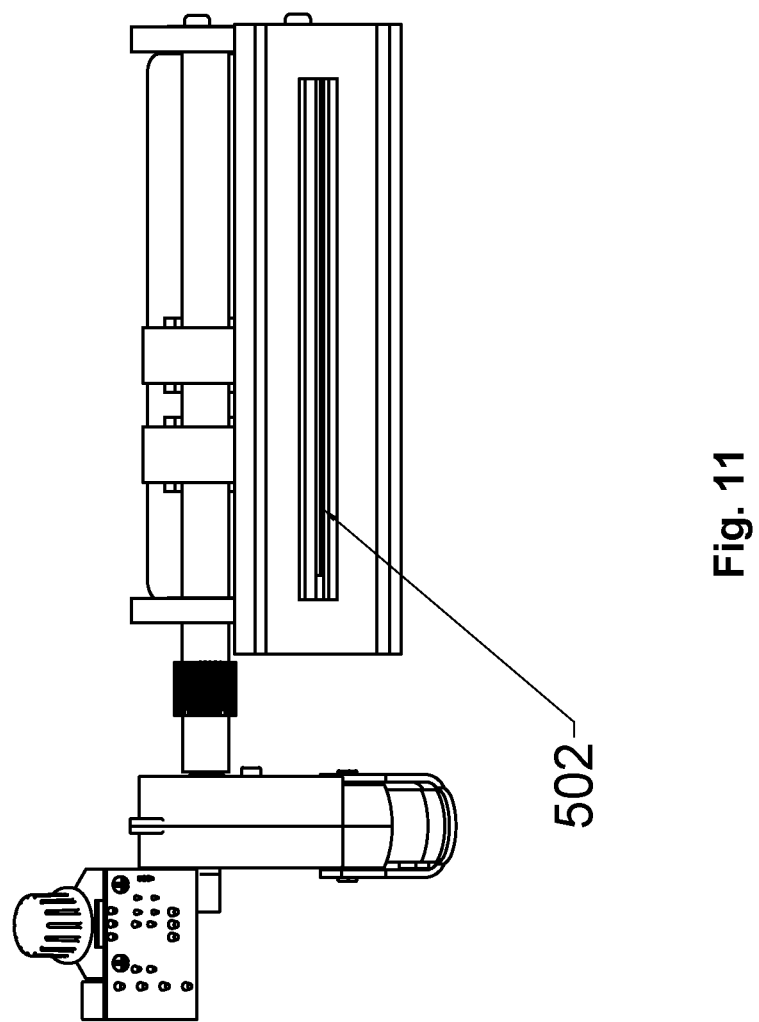
FIG. 11 is a bottom view the roller system of the transactional money sanitizer showing according to an embodiment of the present invention.
Figure 12:
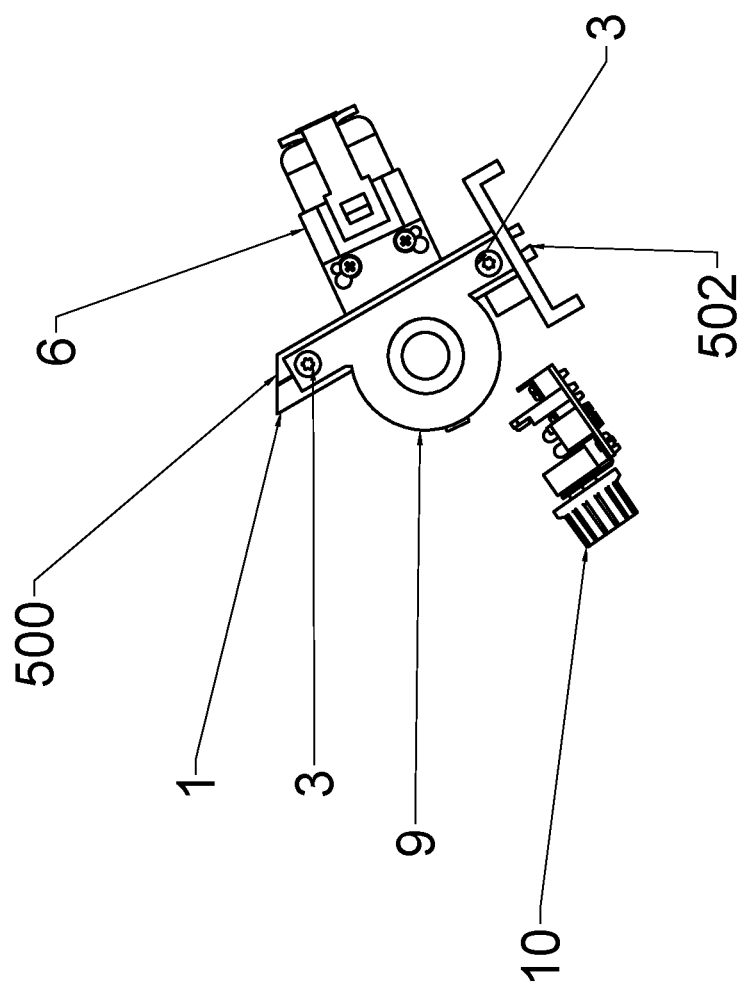
FIG. 12 is a side view the roller system of the transactional money sanitizer showing according to an embodiment of the present invention.

Referring to FIGS. 1 through 7, the present invention is directed to a transactional currency sanitizer (herein described as the "invention") 100. The invention 100 includes an enclosure 270, a deposit device on said enclosure for depositing the currency into the enclosure, an ultraviolet radiation-producing (UV) device 250, a retrieval device on the enclosure for retrieving the currency from the enclosure. The invention 100 also includes a bill sanitizer 200 and a coin sanitizer 230 each with its own linearly aligned deposit and retrieval device.

The invention 100 allows a user to deposit currency into the enclosure 270 via the deposit device which passes the currency between at least two spaced-apart UV light emitters 400 of the UV device 250 to sanitize both sides of the currency. A user then retrieves the sanitized currency from the enclosure 270 via the retrieval device which is configured to accept the sanitized currency from between the at least two spaced-apart UV light emitters 400 and to provide the sanitized currency for retrieval from the enclosure. As used herein, currency refers to both paper money and coins. Paper money may also be referred to as bills. The bill sanitizer 200 may feed an individual bill 902 through the UV device 250 to sanitize both sides of the individual bill 902. The bill sanitizer 200 may deposit the individual bill 902 into the one or more collection drawers 265. The coin sanitizer 230 may feed an individual coin 911 through the UV device 250 to sanitize both sides of the individual coin 911. The coin sanitizer 230 may deposit the individual coin 911 into the one or more collection drawers 265.

The bill sanitizer 200 may comprise a deposit and retrieval roller systems which includes plurality of bill guides, a plurality of feed roller pairs, a bill roller motor 220, and a gear train 221. The plurality of bill guides may direct the individual bill 902 through the bill sanitizer 200 such that both sides of the individual bill 902 are exposed to the UV device 250. The plurality of bill guides may comprise straight or curved shields or chutes that restrict the direction that the individual bill 902 may travel. The individual bill 902 may be conveyed through the bill sanitizer 200 via the plurality of feed roller pairs. When energized, the bill roller motor 220 may cause rotation of the plurality of feed roller pairs via the gear train 221.

An individual feed roller pair selected from the plurality of feed roller pairs may comprise a first roller 208 and a second roller 209. The first roller 208 and the second roller 209 may rotate on parallel axes and may contact each other at a boundary between the first roller 208 and the second roller 209. The first roller 208 and the second roller 209 may be geared to turn in opposite rotational directions such that the individual bill 902 arriving at the boundary between the first roller 208 and the second roller 209 may be conveyed through the individual feed roller pair.

In some embodiments, the path of the individual bill 902 through the bill sanitizer 200 may advance the individual bill 902 from a bill entry aperture 281 located at the rear of the enclosure 270 to a bill exit aperture 272 located above the one or more collection drawers 265 by moving the individual bill 902 through the plurality of bill guides such that the individual bill 902 passes the UV device 250 one or more times. Specifically, the path of the individual bill 902 through the bill sanitizer 200 may comprise passing through an entry bill guide 202, a first feed roller pair 211, an upper bill guide 203, a second feed roller pair 212, a forward bill guide 204, a third feed roller pair 213, the UV device 250, a fourth feed roller pair 214, a rear bill guide 205, a fifth feed roller pair 215, and through the bill exit aperture 272 into the one or more collection drawers 265.

The entry bill guide 202 may direct the individual bill 902 through the bill entry aperture 281 and into the first feed roller pair 211. The first feed roller pair 211 may propel the individual bill 902 towards the front of the bill sanitizer 200 and into the upper bill guide 203. The upper bill guide 203 may direct the individual bill 902 into the second feed roller pair 212. The second feed roller pair 212 may propel the individual bill 902 forwards and into the forward bill guide 204. The forward bill guide 204 may bend the path of the individual bill 902 downwards and rearwards such that the individual bill 902 reverses direction and begins travelling towards the rear of the bill sanitizer 200 and into the third feed roller pair 213. The third feed roller pair 213 may propel the individual bill 902 rearwards such that the individual bill 902 passes the UV device 250 and into the fourth feed roller pair 214. The fourth feed roller pair 214 may propel the individual bill 902 rearwards into the rear bill guide 205. The rear bill guide 205 may bend the path of the individual bill 902 downwards and forwards such that the individual bill 902 is directed into the fifth feed roller pair 215. The fifth feed roller pair 215 may propel the individual bill 902 through the bill exit aperture 272 and into the one (1) or more collection drawers 265.

The gear train 221 may comprise one (1) or more gears. Individual gears selected from the one (1) or more gears may be coupled to the shaft of the bill roller motor 220, to the first roller 208 of each of the plurality of feed roller pairs, and to the second roller 209 of each of the plurality of feed roller pairs. The remainder of the one (1) or more gears may serially mesh to transmit rotation of the shaft of the bill roller motor 220 to the first roller 208 and the second roller 209 of each of the plurality of feed roller pairs. The one (1) or more gears may assure that the first roller 208 and the second roller 209 in each of the plurality of feed roller pairs are rotating at the same speed and in opposite rotational directions.

The coin sanitizer 230 may comprise a coin collection bin 231, a coin retrieval slide 236, a cam motor 235, a cam wheel 233, a vibration chute 238, and a coin exit slide 240. The coin collection bin 231 may retain coins that are deposited into the coin sanitizer 230 via a coin entry aperture 283. The coins may be removed from the coin collection bin 231 one (1) at a time by the coin retrieval slide 236 located at the bottom of the coin collection bin 231. The individual coin 911 removed from the coin collection bin 231 by the coin retrieval slide 236 may fall onto the vibration chute 238. The individual coin 911 may pass the UV device 250 as the individual coin 911 slides down the vibration chute 238 onto the coin exit slide 240. The coin exit slide 240 may direct the individual coin 911 into the one (1) or more collection drawers 265 via a coin exit aperture 273.

The coin retrieval slide 236 may be slidably coupled to the coin collection bin 231 at the bottom of the coin collection bin 231. The coin retrieval slide 236 may be inserted into the coin collection bin 231 through a slot on a side of the coin collection bin 231. The coin retrieval slide 236 may move laterally within the coin sanitizer 230 between a loading position and an unloading position. When in the loading position, the coin retrieval slide 236 may be pushed into the coin collection bin 231 such that the individual coin 911 may fall into a coin retrieval aperture 232 located on the coin retrieval slide 236. In the loading position, the individual coin 911 may be prevented from exiting through the bottom of the coin retrieval aperture 232 by the bottom of the coin collection bin 231. When in the unloading position, the coin retrieval slide 236 may be withdrawn through the side of the coin collection bin 231 such that the coin retrieval aperture 232 is outside of the coin collection bin 231. In the unloading position, the individual coin 911 is free to fall from the coin retrieval aperture 232 onto the vibration chute 238.

When energized, the cam motor 235 may cause a reciprocating motion of the coin retrieval slide 236. Specifically, rotation of the cam motor 235 may cause rotation of the cam wheel 233 which is coupled to the cam motor 235. One (1) end of a cam arm 234 may be pivotably coupled to the cam wheel 233 and may following a circular path when the cam motor 235 is energized. The opposite end of the cam arm 234 may be pivotably coupled to the coin retrieval slide 236 and may follow a reciprocating linear path when the cam motor 235 is energized, thus causing a reciprocating motion of the coin retrieval slide 236. As a non-limiting example, the cam arm 234 may couple to the coin retrieval slide 236 via a cam pin 239.

The UV device 250 may produce illumination within the ultraviolet portion of the spectrum when the UV lamp 250 is energized. In some embodiments, the illumination may lie within the UV-C portion of the spectrum. UV-C, with wavelengths between one hundred to two hundred eighty nanograms (100 nm-280 nm), may have germicidal properties making UV-C effect in destroying bacteria, viruses, mold, and fungi. As non-limiting examples, the UV device 250 may comprise one (1) or more fluorescent tubes, one (1) or more UV-C LED's, or other sources of UV-C illumination. When the UV device 250 is based upon fluorescent tube technology, the invention 100 may comprise a lamp ballast 252 for starting the UV device 250. The UV device 250 may detachably couple to a lamp base 251.

In some embodiments, the UV device 250 may have U-shaped light emitters such that paper money and the coins may pass through a central gap 253 of the UV lamp 250. By passing through the central gap 253, the paper money and the coins may be exposed to ultraviolet illumination on both sides simultaneously. Alternatively, the UV device 250 may comprise two (2) parallel illumination emitters 400 with the central gap 253 between the two parallel illumination emitters.

One (1) or more electronic boards 255 may control operation of the bill sanitizer 200 and the coin sanitizer 230. As non-limiting examples, the one (1) or more electronic boards 255 may determine when to energize and de-energize the bill roller motor 220, when to energize and de-energize the cam motor 235, and when to energize and de-energize the UV device 250. As non-limiting examples, the one (1) or more electronic boards 255 may make determinations to energize or de-energize based upon inputs from one (1) or more bill sensors located at the bill entry aperture 281, one (1) or more coin sensors located at the coin entry aperture 283, user-operated controls such as switches or push buttons, timer circuits within the one (1) or more electronic boards 255, or combinations thereof.

A power supply 260 may convert an AC input voltage into AC and/or DC voltage levels required for operation by the one (1) or more electronic boards 255, the bill roller motor 220, the cam motor 235, and the UV device 250.

The one (1) or more collection drawers 265 may removably reside in the bottom of the enclosure 270 and may be accessible via a drawer aperture 284 on the front of the enclosure 270. The one (1) or more collection drawers 265 may collect the paper money and the coins after the paper money and the coins have been sanitized by exposure to the UV device 250. The one (1) or more collection drawers 265 may be positioned beneath the bill exit aperture 272 to catch the paper money exiting the bill sanitizer 200 and beneath the coin exit aperture 273 to catch the coins exiting the coin sanitizer 230. In some embodiments, the one (1) or more collection drawers 265 may comprise one (1) or more dividers 266 to separate the paper money and the coins.

The enclosure 270 may house the bill sanitizer 200, the coin sanitizer 230, the UV device 250, the power supply 260, and the one (1) or more electronic boards 255 and may be adapted to protect people from exposure to moving parts and ultraviolet illumination. The enclosure 270 may comprise a cover 280 and a support frame 271. The cover 280 may comprise an outer shell for the invention 100. The cover 280 may comprise the bill entry aperture 281, the coin entry aperture 283, and the drawer aperture 284. The bill entry aperture 281 may be an opening on the rear side of the cover 280 through which the paper money may be inserted into the bill sanitizer 200. In some embodiments, the bill entry aperture 281 may be covered by a bill entry door 282 which may be removable or hinged to the cover 280. The coin entry aperture 283 may be an opening on the rear side of the cover 280 through which the coins may be inserted into the coin sanitizer 230. The drawer aperture 284 may be an opening on the front side of the cover 280 through which the one or more collection drawers 265 may be inserted and removed.

In some embodiments, a hinge 285 may enable a front portion of the cover 280 to be lifted while a rear portion of the cover 280 remains coupled to the side of the cover 280 so that the bill sanitizer 200 and the coin sanitizer 230 may be accessed for servicing.

The support frame 271 may comprise structural elements located within the cover 280 that are used to retain and guide the one or more collection drawers 265, the bill sanitizer 200, the coin sanitizer 230, the power supply 260, and the lamp ballast 252. The support frame 271 may support the bill sanitizer 200 and the coin sanitizer 230 above the one (1) or more collection drawers 265. The support frame 271 may guide the one (1) or more collection drawers 265 as the one (1) or more collection drawers 265 slide in and out of the enclosure 270. The support frame 271 may comprise the bill exit aperture 272 through which the paper money may pass from the bill sanitizer 200 to the one (1) or more collection drawers 265. The support frame 271 may comprise the coin exit aperture 273 through which the coins may pass from the coin sanitizer 230 to the one (1) or more collection drawers 265.

Referring to FIGS. 8 to 12, in one embodiment, the roller system two consists of a money drop 1, two TPU pinch rollers 7,8 one DC geared motor 6 with gear motor box 6, roller cap 5, an acrylic roller 4, four torx screws 3, two stainless steel roller bearings 2, and two pillow bearings 9 to hold the roller bearings 2. This roller system solves the problem of moving thin sheets of paper or plastic that are of variable levels of quality and thickness. Specifically, it allows the fluid movement of materials that are torn, folded, or crumpled in such a fashion that it doesn't produce any type of hindrance to the flow of the aforementioned materials.

With the DC motor 6 on, the paper or plastic item is inserted at the opening 500 of the money drop 1 so it's gravity fed. It then proceeds to be pinched by two TPU rollers 7, 8. There, an acrylic roller shaft 4 and the DC motor 6 turns the acrylic roller 4 clockwise with the TPU pinch rollers 7, 8. The acrylic roller 4 is secured by the roller cap 5 and two pillow bearings 9 with roller bearings 2 that allows axial shaft rotation. The flexible plastic TPU properties enables thin pieces of paper and plastic to slide into the roller system and be pushed out the exit 502 of the money drop 1. Paper and plastic sheets are pinched between the TPU rollers 7,8 and the inside wall 503 of the money drop 1. This enables the material to slide along the inside wall due to the clockwise rotation of the TPU pinch rollers 7, 8 on the acrylic shaft 4 without damaging the paper or plastic. The flexibility of the TPU material allows paper and plastic ranging from 0.004 inches to 0.020 inches in thickness to moved within the money drop 1. This uniquely allows variability in the paper and plastic material dimensions so that variably sized materials do not inhibit the functionality of the roller system. Additionally, it can be done even with folded, torn, or bent corners on the paper items. The DC motor control is done with the motor controlling driver 10 and the DC motor gearbox 6 provides adequate torque to move small paper notes through the money drop 1. The four torx screws 3 are attached to the pillow bearing bodies 9 on each side of the money drop 1. The torque screws 3 can be tightened or loosened to control the amount of runout on the acrylic shaft 4 which allows customization in the gap between the TPU pinch rollers 7,8 and the inside wall of the money drop 1. This customizable gap allows even more space between the TPU pinch rollers 7,8 and the inner wall of the money drop 1.

Figure 13:
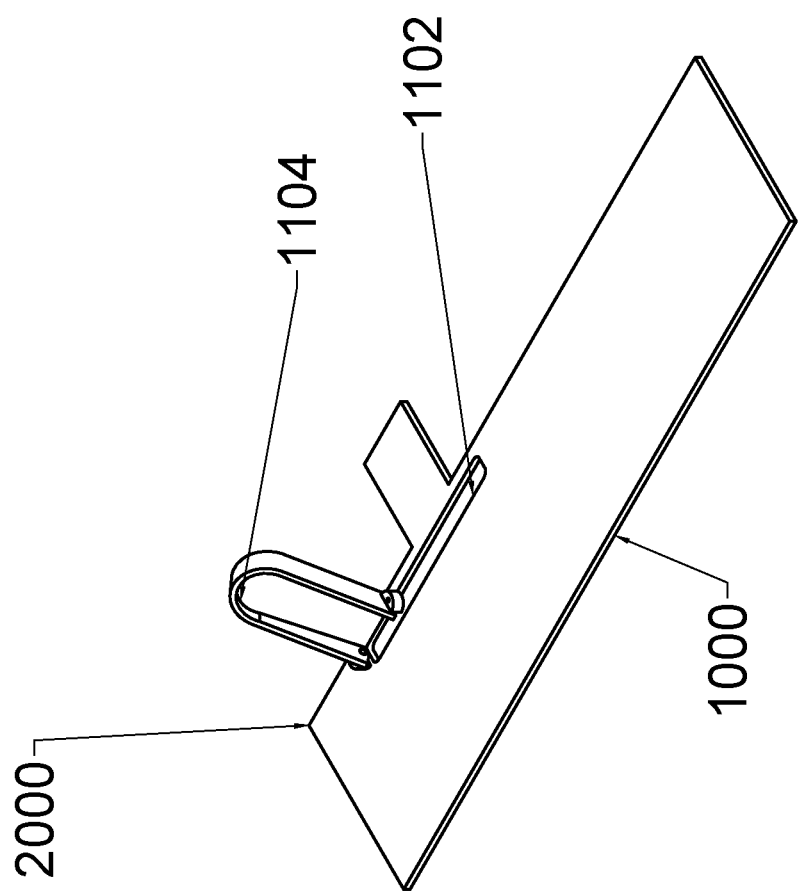
FIG. 13 is an isometric view of a coin drop of the transactional money sanitizer showing according to an embodiment of the present invention.
Figure 14:
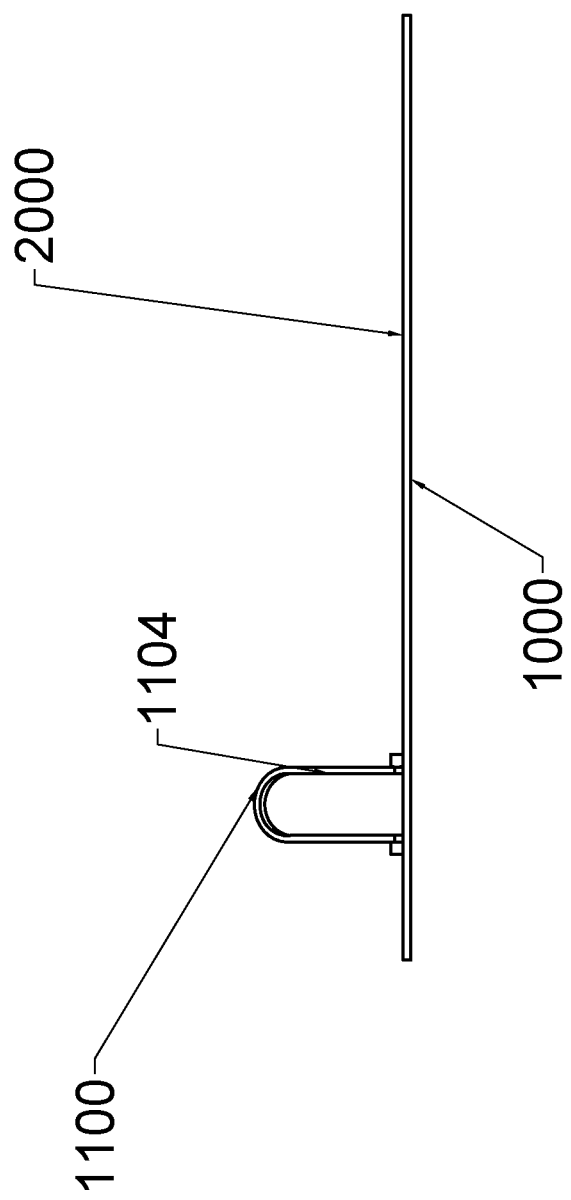
FIG. 14 is a front view of the coin drop of the transactional money sanitizer showing according to an embodiment of the present invention.

Referring to FIGS. 13 to 14, in one embodiment, the coin drop 1000 is fastened directly to top plate 2000 of the invention 100. It is specifically angled at a 60-degree angle to allow the coin to be inserted at the top of the coin drop 1100 and to slide directly into the money slot 1102. From the money slot the coins will descend into the money drop 9 and the coins will descend by gravity through the UV device 250. The coin drop 1100 is designed with the intent to allow anything the size of US quarter or smaller to slide with great ease into the money slot. This gravity fed delivery will provide contactless delivery of coin currency and exchange. The coin drop 1100 has a tapered ramp 1104 to assist in the function alignment of the money drop. And this also allows the coin to be put into a shallow position and slide deeper into the design as it gets closer to the critical point where it inserts into the actual money drop 9. This creates great coin alignment with the openings of the money slot to provide a rapid pass through the intervention 100.

Figure 15:
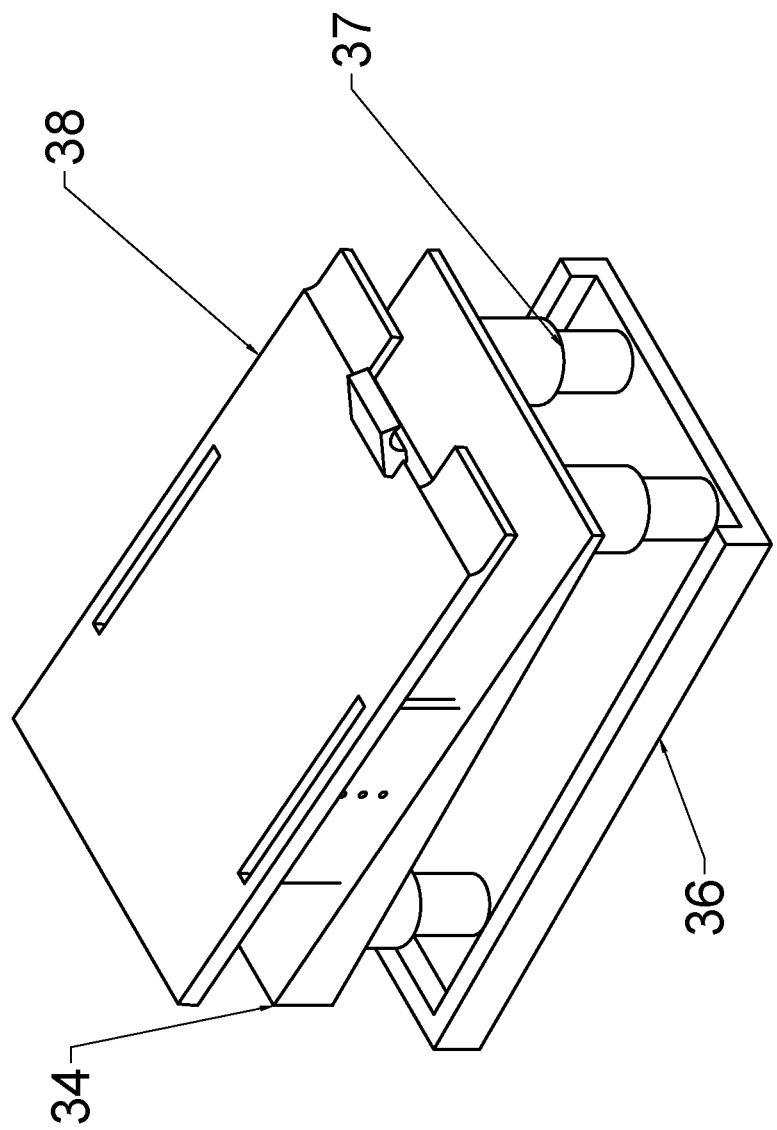
FIG. 15 is an isometric view of a bill tray of the transactional money sanitizer showing according to an embodiment of the present invention.
Figure 16:
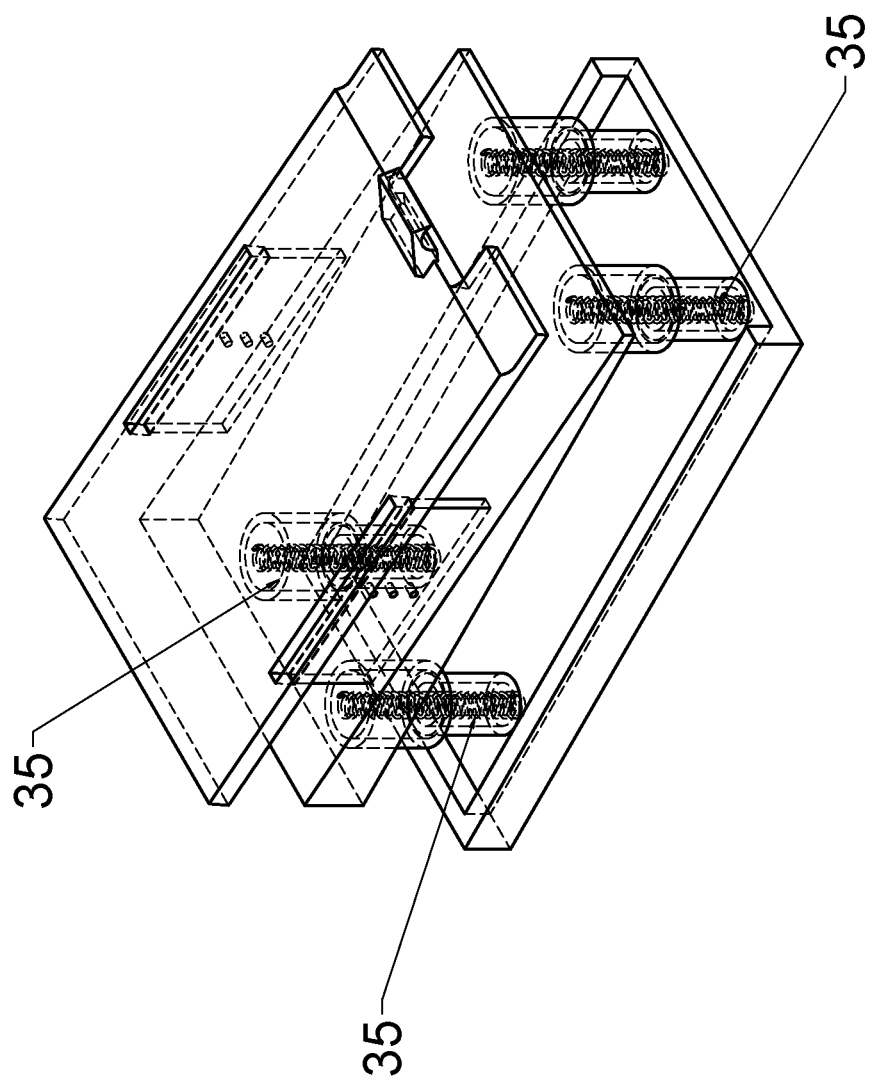
FIG. 16 is an isometric view showing hidden lines of the bill tray of the transactional money sanitizer showing according to an embodiment of the present invention.

Referring to FIGS. 15 and 16, a bill tray 34 may be provided that is a compression spring loaded device consisting of multiple parts that compress against various polymer bills and paper notes. The guide 36, bill platform 37, and tab work 38 together to organize, stack, and guide the bank notes. This is done to create a simple slide action that allows paper money or polymer notes to be processed through the money drop 9 of the invention 100. Inside the money tray 34 are four compression springs 35 that allow spring loaded action to compress the paper notes or polymer bills to allow rapid feeding into the money drop 9. The aforementioned bills are fed individual using a gear and roller system powered by direct current (DC) motors 44.

The DC motors are controlled by a processor and touchscreen. The notes are fed through the money drop 9 and in turn are sanitized by UVC device 250 at 254 nanometer wavelengths. The specific feeding area allows the bank notes and coin money to fed through the UV device 250 allowing simultaneous cleaning of both sides of the inputted object.

Figure 17:
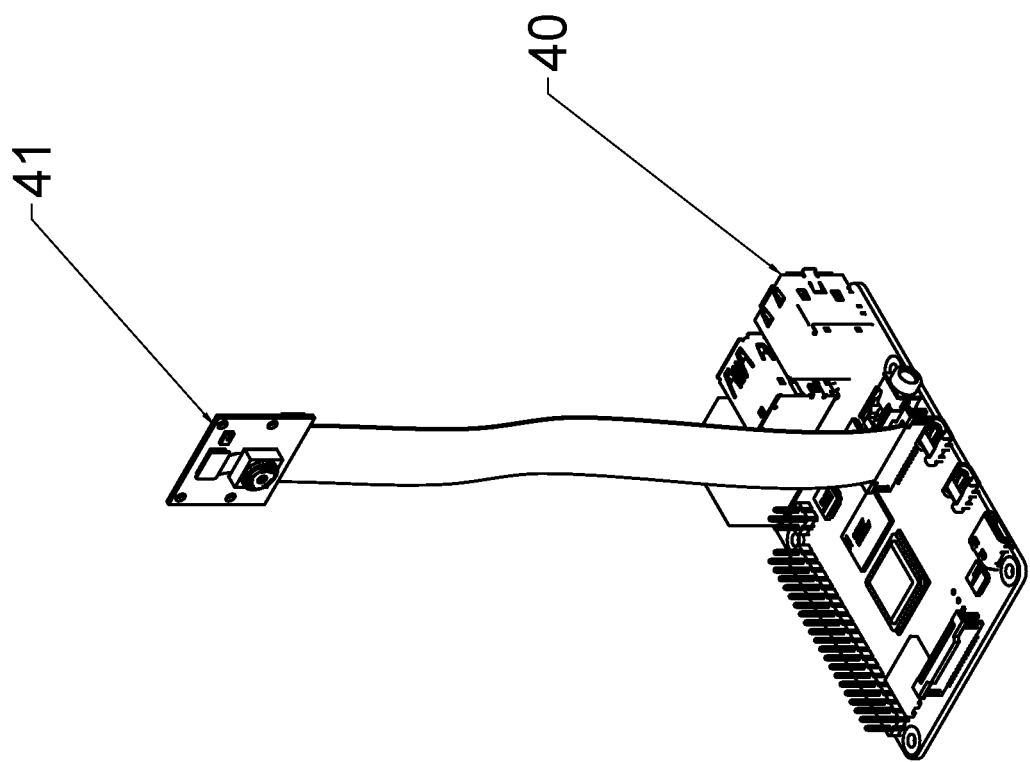
FIG. 17 is an isometric view of a camera and processor of the transactional money sanitizer showing according to an embodiment of the present invention.

The UV device 250 is able to cleanse 24 square inches a second of surface area in order to inactivate certain types of viruses. The money continues to descend in the UV device 250, fed by gravity, and it drops into one or more collection drawers 265. One or more collection drawers 265 are lined with polyurethane foam that allows a safe and quiet landing for any type of money. Drawer 265 is secured with a lock and key that is only accessible to someone who has the key. The invention 100 then begins its secondary process: machine learning (ML) using artificial intelligence (AI) for countering the distribution of counterfeit bank notes. The ML emanates from Raspberry Pi (RPI) MCU processor 40 equipped with the Pi camera 41 for high resolution (1080HP) as shown in FIG. 17. The invention 100 is equipped with open source software that has been trained sufficiently to count currency and to detect counterfeit bills via Pi camera 41. This is done using the refraction of UV rays on a paper note or polymer bill caught on the Pi camera 41. The RPI Pi camera 41 is equipped to detect the color changes in the bill that would be a positive correlation of a counterfeit bill. The ML software alerts the user that a bill has been placed inside the invention 100 is not a valid banknote. The touchscreen GUI has a notification that notifies the user that the bill has been deposited in the drawer 265. The drawer 265 is able to be removed from the invention 100 using a lock and key method. The unlocked drawer is removable from the front or the back and allows the user to switch off the UV device 250 before removing any money. Then the counterfeit bill can be extracted from the drawer 265 manually to prevent the transfer of counterfeit money. The purpose of the machine learning for anti-counterfeiting is to prevent the use of the machine to clean unauthorized banknotes and or currency.

Figure 18:
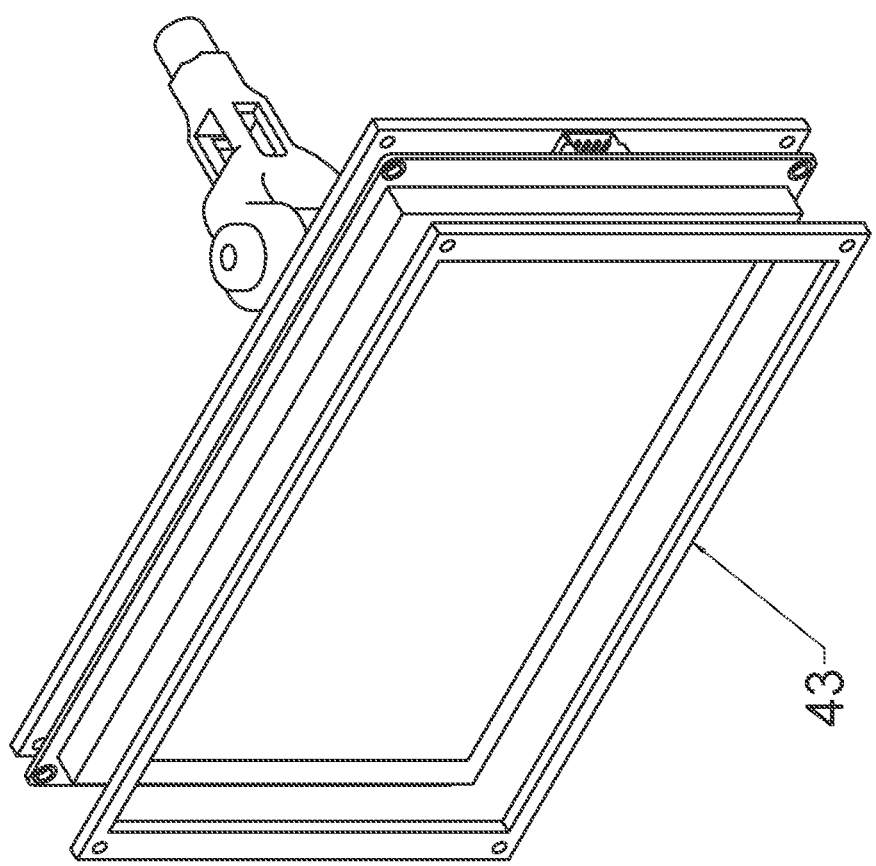
FIG. 18 is an isometric view of a touch screen device of the transactional money sanitizer showing according to an embodiment of the present invention.

The invention 100 has a plug-in processor 40 that controls the invention's 100 various components, for example, fans, touchscreen, DC motors 44, UV device 250, and other electronic equipment with a 12 Volt power supply 29. Fans allow rapid cooling to the UV device 250 and also for the removal of ozone and are controlled with the 7-inch touchscreen 43 (FIG. 18) using a specialized graphical user interface (GUI) that allows the user to toggle the fans off or on. Through the touchscreen 43 various diagnostics, status checks, and custom features of the invention 100 can be done remotely or by serial port. Invention 100 also has a virtual internet dashboard that is accessible through the Cloud and has also been uploaded into the touchscreen GUI. The software, dashboard, and touchscreen 43 can be customized to achieve other design functions. Namely, the dashboard capabilities and the machine learning capabilities of the design making this unit totally configurable for of plethora of applications. These capabilities include machine learning, artificial intelligence, preventive maintenance, and safe electronic deployment.

Operation

A user will have to plug in a three-pronged plug to a conventional electrical outlet to activate the invention 100. The UV device 250 is set up with a light cord and switch system on a relay module that is connected to a processor. For the UV device 250 to be activated it first must be plugged in and the switch must be turned on. The processor has power via a USB connection to a power source. Once the processor is activated, and the touchscreen is activated, the UV device 250 will turn on after a three second safety feature is lapsed. During that light activation time the UV device 250 will stay on for at least one minute. After one minute it will turn off as a safety feature to prevent any type of overheating to the unit. While the UV device 250 is activated the bill 200 and coin 230 sanitizers are loaded with paper or polymer bank notes.

In use, paper money may be fed into a bill entry aperture 281 located on the rear of the invention 100. An individual bill 902 may pass a UV device 250 as the individual bill 902 is directed through a bill sanitizer 200 by a plurality of feed roller pairs and a plurality of bill guides. Exposure to ultraviolet illumination may sterilize the individual bill 902. The individual bill 902 may be deposited into one (1) or more collection drawers 265 after passing through the bill sanitizer 200. Coins may be fed into a coin entry aperture 283 located on the rear of the invention 100 and may land in a coin collection bin 231. An individual coin 911 may be retrieved from the coin collection bin 231 by the reciprocating motion of a coin retrieval slide 236 and may be dropped onto a vibration chute 238. The individual coin 911 may slide down the vibration chute 238, may pass the UV device 250, and may be directed into the one or more collection drawers 265 by a coin exit slide 240. Exposure to ultraviolet illumination may sterilize the individual coin 911. The individual coin 911 may be deposited into the one (1) or more collection drawers 265 after passing through a coin sanitizer 230. The one (1) or more collection drawers 265 may be removed from the front of the invention 100, emptied, and then returned to the invention 100.

The invention 100 is not limited to the described embodiment, and a person skilled in the art will appreciate that many other embodiments of the invention are possible without deviating from the basic concept of the invention and that any such work around will also fall under scope of this invention. It is envisioned that other styles and configurations of the present invention can be easily incorporated into the teachings of the present invention, and only one (1) particular configuration shall be shown and described for purposes of clarity and disclosure and not by way of limitation of scope. All of the implementations described below are exemplary implementations provided to enable persons skilled in the art to make or use the embodiments of the disclosure and are not intended to limit the scope of the disclosure, which is defined by the claims. The terms "a" and "an" herein do not denote a limitation of quantity, but rather denote the presence of at least one (1) of the referenced items.

The exact specifications, materials used, and method of use of the invention 100 may vary upon manufacturing. The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

While embodiments of the invention have been described and illustrated, such embodiments should be considered illustrative of the invention only. The invention may include variants not described or illustrated herein in detail. Thus, the embodiments described and illustrated herein should not be considered to limit the invention as construed in accordance with the accompanying claims.

What is claimed is:

1. A transactional currency sanitizer, comprising:
   an enclosure;
   a deposit device on said enclosure for depositing the currency into said enclosure;
   an ultraviolet radiation-producing (UV) device inside of said enclosure, said UV device comprising at least two spaced-apart UV light emitters;
   a retrieval device on said enclosure for retrieving the currency from said enclosure;
   wherein said deposit device is configured to receive the currency and pass the currency between said at least two spaced-apart UV light emitters to sanitize both sides of the currency; and
   wherein said retrieval device is configured to accept said sanitized currency from between said at least two spaced-apart UV light emitters and to provide said sanitized currency for retrieval from said enclosure.

2. The transactional currency sanitizer of claim 1 wherein said deposit device comprises an opening on said enclosure and a deposit chute cooperating with said opening and operable to pass the currency between said at least two spaced-apart UV light emitters.

3. The transactional currency sanitizer of claim 2 wherein said retrieval device comprises an exit on said enclosure and a retrieval chute linearly aligned with said deposit chute and opposite from said UV device, said retrieval chute operable to retrieve said sanitized currency after exiting said UV device and providing said sanitized currency to said exit.

4. The transactional currency sanitizer of claim 3 wherein said exit comprises a collection drawer operable in two states, a first state being an open state for a user to open and retrieve said sanitized currency and a second state being a closed state to safely store said sanitized currency inside said enclosure.

5. The transactional currency sanitizer of claim 4 wherein said collection drawer includes a locking device.

6. The transactional currency sanitizer of claim 1 wherein said deposit device comprises an opening on said enclosure and a deposit roller system cooperating with said opening and operable to pass the currency between said at least two spaced-apart UV light emitters.

7. The transactional currency sanitizer of claim 6 wherein said retrieval device comprises an exit on said enclosure and a retrieval roller system linearly aligned with said deposit roller system and opposite from said UV device, said retrieval roller system operable to retrieve said sanitized currency after exiting said UV device and providing said sanitized currency to said exit.

8. The transactional currency sanitizer of claim 7 wherein both of said deposit and retrieval roller systems are configured to accept multiple pieces of currency.

9. The transactional currency sanitizer of claim 7 wherein said exit comprises a collection drawer operable in two states, a first state being an open state for a user to open and retrieve said sanitized currency and a second state being a closed state to safely store said sanitized currency inside said enclosure.

10. The transactional currency sanitizer of claim 1 further comprising a currency calculator inside of the said enclosure.

11. The transactional currency sanitizer of claim 10 wherein said currency calculator comprises a high-speed camera in communication with a processor, said processor comprising artificial intelligence (AI) software operable to determine various denominations of currency and calculating a total value of currency being sanitized.

12. The transactional currency sanitizer of claim 11 wherein said AI software is also operable to detect counterfeit currency.

13. The transactional currency sanitizer of claim 11 wherein said enclosure further comprises a WiFi transponder in communication with said processor.

14. The transactional currency sanitizer of claim 11 wherein said enclosure further comprises an exterior controller in communication with said processor for operating the currency sanitizer.

15. The transactional currency sanitizer of claim 14 wherein said exterior controller comprises a touch screen device.

16. The transactional currency sanitizer of claim 1 wherein said enclosure further comprises a service door for maintenance of the currency sanitizer.

17. The transactional currency sanitizer of claim 16 wherein said service door is configured for locking and unlocking.

18. A transactional currency sanitizer, comprising:
a bill sanitizer;
a coin sanitizer;
an ultraviolet radiation-producing (UV) device, said UV device comprising at least two spaced-apart UV light emitters;
at least one collection drawer; and
an enclosure;
wherein said bill sanitizer is capable of directing an individual bill of currency through said at least two spaced-apart UV light emitters to sanitize both sides of said individual bill of currency;
wherein said bill sanitizer is capable of depositing said the individual bill of currency into an individual collection drawer;
wherein said coin sanitizer is capable of directing an individual coin of currency through said at least two spaced-apart UV light emitters to sanitize both sides of said individual coin of currency; and
wherein said coin sanitizer is capable of depositing said the individual coin of currency into another individual collection drawer.

19. The transactional currency sanitizer of claim 18 further comprising a currency calculator inside of the said enclosure.

20. The transactional currency sanitizer of claim 19 wherein said currency calculator comprises a high-speed camera in communication with a processor, said processor comprising artificial intelligence (AI) software operable to determine various denominations of currency and calculating a total value of currency being sanitized.

21. The transactional currency sanitizer of claim 20 wherein said AI software is also operable to detect counterfeit currency.

22. The transactional currency sanitizer of claim 20 wherein said enclosure further comprises a WiFi transponder in communication with said processor.

23. The transactional currency sanitizer of claim 20 wherein said enclosure further comprises an exterior controller in communication with said processor for operating the currency sanitizer.

24. The transactional currency sanitizer of claim 23 wherein said exterior controller comprises a touch screen device.

25. The transactional currency sanitizer of claim 18 wherein said at least one collection drawer includes a locking device.

26. The transactional currency sanitizer of claim 18 wherein said enclosure further comprises a service door for maintenance of the currency sanitizer.

27. The transactional currency sanitizer of claim 26 wherein said service door is configured for locking and unlocking.

* * * * *